US00PP11626P

United States Patent [19]

Olesen et al.

[11] Patent Number: Plant 11,626

[45] Date of Patent: Nov. 7, 2000

[54] COMPACT FLORIBUNDA ROSE PLANT NAMED 'POULZIN'

[75] Inventors: L. Pernille Olesen; Mogens N. Olesen, both of Fredensborg, Denmark

[73] Assignee: Poulsen Roser, ApS, Fredensborg, Denmark

[21] Appl. No.: 09/173,863

[22] Filed: Oct. 16, 1998

[51] Int. Cl.[7] ..... A01H 5/00

[52] U.S. Cl. ..... Plt./150

[58] Field of Search ..... Plt./141, 150, 151, Plt./123, 129

*Primary Examiner*—Howard J. Locker

[57] ABSTRACT

A new compact floribunda rose plant which has abundant, cherry-red flowers and attractive foliage. The variety successfully propagates from softwood cuttings and traditional budding and is suitable for production in commercial glasshouses and nurseries. This new and distinct variety has shown to be uniform and stable in the resulting generations from asexual propagation.

1 Drawing Sheet

SUMMARY OF THE INVENTION

The present invention constitutes a new and distinct variety of compact floribunda rose plant which originated from a controlled crossing between 'Dalli Dalli' and an unnamed seedling. The two parents were crossed and the resulting seeds were planted in a controlled environment. The new variety is named 'POULzin'.

The new rose may be distinguished from its seed parent, 'Dalli Dalli', by the following combination of characteristics:

1. 'POULzin' is a compact floribunda rose with cherry-red flowers while 'Dalli Dalli' is a floribunda with bright orange-red flowers.

2. 'Dalli Dalli' is taller in height than 'POULzin'.

The new variety may be distinguished from its pollen parent, unnamed seedling created by the same inventors, by the following combination of characteristics:

1. The unnamed seedling is a Palace rose with soft pink flowers, and 'POULzin' is a compact floribunda rose with cherry-red flowers.

The objective of the hybridization of this rose variety for commercial greenhouse culture was to create a new and distinct variety with unique qualities, such as:

1. Uniform and abundant flowers;

2. Vigorous and compact growth;

3. Year-round flowering under glasshouse conditions;

4. Suitability for production from softwood cuttings in pots;

5. Durable flowers and foliage which make a variety suitable for distribution in the floral industry.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULzin' was selected by the inventors as a single plant from the progeny of the hybridization in February, 1992.

Asexual reproduction of 'POULzin' by cuttings and traditional budding was first done by L. Pernille and Mogens N. Olesen in their nursery in Fredensborg, Denmark in May, 1992. This initial and other subsequent propagations conducted in controlled environments have demonstrated that the characteristics of 'POULzin' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULzin'. Specifically illustrated in SHEET 1:

1. Stem showing branching and the attachment of leaves, buds, and peduncles;

2. Flower bud, partially opened bud, and open bloom;

3. Flower petals, detached;

4. Sepals, receptacle, and pedicel;

5. Flowering stem;

6. Leaves.

DETAILED DESCRIPTION OF THE VARIETY

The following is a detailed description of 'POULzin', as observed in its growth in glasshouses in Fredensborg, Denmark and Half Moon Bay, Calif. Color references are made using The Royal Horticultural Society (London, England) Colour Chart, 1995, except where common terms of color are used.

A comparison variety is 'POULrek', a patented variety by the same inventors described and illustrated in U.S. Plant Pat. No. 9,688 and issued on Nov. 12, 1996. Chart 1 details several physical characteristics of 'POULzin' and 'POULrek'.

CHART 1

| | 'POULzin' | 'POULrek' |
|---|---|---|
| Flower bud when sepals first divide | Red-Purple Group 57C | Red Group 36C and Yellow-Orange Group 23C |
| Flower bloom, petal - Upper surface | Red Group 45B - Red-Purple Group 57C | Red Group 36D |
| Flower bloom, petal - Reverse surface | Red-Purple Group 57C | Red Group 36D |

Parents: 'Dalli Dalli'×Unnamed seedling.

Classification:

*Botanical.*—Rosa hybrida.

*Commercial.*—Compact floribunda.

FLOWER AND FLOWER BUD

Blooming habit: Recurrent.

Flower bud:

*Size.*—Upon opening, 22 mm–24 mm in length from base of receptacle to flower tip.

*Bud form.*—Ovoid to globular.

*Bud color.*—As sepals unfold, Red-Purple Group 57C. Red-Purple Group 57C at ¼ opening.

*Sepals.*—Green Group 143A. On plants grown in full sun, sepals with intonation of Greyed-Red 180A. Weak foliaceous appendages and a limited number of marginal stiptitate glands on three of the five sepals. Surfaces of other sepals lightly pubescent.

*Stipitate glands.*—Limited numbers on some sepal margins.

*Peduncle.*—Surface: Smooth, with a limited number of stipitate glands. Length: 35–45 mm average length. Color: Green Group 138B–143A. On plants grown under high light conditions, peduncle may exhibit intonations of Greyed-Red Group 181A. Strength: Upright.

*Receptacle.*—Surface: Smooth, glabrous. Shape: Broadly urn-shaped. Size: Small to medium. 7 mm (h)×5 mm (w). Color: Green Group 138B–143A.

*Borne.*—Singly and in small clusters.

Flower bloom:

*Size.*—Medium for a 15 cm pot rose. Average diameter is 50 mm–60 mm when open.

*Form.*—Shape of flower when viewed from the side: Upon opening, upper part: Flattened convex. Upon opening, lower part: Convex. Open flower, upper part: Convex. Open flower, lower part: Concave.

*Petals.*—Reflexing. Petals not persisting upon senescence.

*Petalage.*—Very double. Average range: Over 60 petals under normal conditions with 5–10 petaloids.

Color:

*Upon opening.*—Petals: Upper Surface: Red Group 45B to Red-Purple Group 57B. Reverse Side: Red-Purple Group 57B.

*After opening.*—Petals: Upper Surface: Red Group 45B to Red-Purple Group 57C. Reverse Side: Red-Purple Group 57C.

Petal spots:

*Upon opening.*—Petals: Outer Side: Green-White Group 157C. Inner Side: Green-White Group 157B.

*After opening.*—Petals: Outer Side: Green-White Group 157C. Inner Side: Green-White Group 157B.

General tonality: No change in the general tonality at the end of the third day. Afterwards, general tonality is Red Group 45C to Red-Purple Group 57C.

Petals:

*Petal reflex.*—Petals reflex backwards somewhat. Some outer petals double reflexed.

*Petal edge.*—Weak undulation.

*Petaloids.*—Present. Generally 5–10 petaloids.

*Fragrance.*—Little or no fragrance.

*Duration.*—As a pot plant, flowers last from 8 to 10 days. As a cut flower 6 to 8 days.

*Texture.*—Average.

*Shape.*—Round to deltoid.

*Form.*—Recurved.

*Arrangement.*—Imbricated.

Reproductive organs: On fully open blooms, reproductive organs generally visible.

*Pollen.*—Color: Yellow-Orange Group 16B. Abundance: Average.

*Anthers.*—Color: Yellow-Orange Group 16B. Size: Small.

*Filaments.*—Color: Yellow Group 11A-B.

*Stigmas.*—Stigmas superior in location to anthers. Color: Yellow Group 11A-B.

*Styles.*—Color: Yellow Group 11A-B.

*Hips.*—None observed.

PLANT

Plant growth: Vigorous, compact, upright to bushy. When grown as a 15 cm pot plant, the average height of the plant itself is to 20–22 cm and the average width is 22 cm. When grown as a nursery plant on its own roots the average plant height is 55–65 cm and the average plant width is 60–65 cm.

Stems:

*Color.*—Young wood: Green Group 138A. Older wood: Green Group 138A.

*Prickles.*—Incidence: Moderate. Size: Average length: 5 mm–7 mm. Color: Young: Yellow-Green Group 145D. Older: Greyed-Orange Group 173D. Shape: Linear to straight with broad base.

*Bark.*—Young wood: Smooth. Older wood: Smooth.

Plant foliage: Normal number of leaflets on normal leaves in middle of the stem: 5–7 leaflets.

*Leaf size.*—Small to medium. 70–80 mm (1)×50 mm (w).

*Abundance.*—Limited to average.

*Color.*—Upper Leaf Surface: Green Group 137A. Lower Leaf Surface: Green Group 138B. Juvenile foliage: Green Group 137A with intonations on leaflet margins and lower leaflet surfaces, petioles, rachis, and stems of Greyed-Red Group 180B.

Plant leaves and leaflets:

*Stipules.*—Bearded. Extensions can be up to 5–6 mm. Margins with a limited numbers of stipitate glands. Size: 8 mm –10 mm. Color: Green Group 137B.

*Petiole.*—Length: 15 mm. Color: Green Group 137B with some intonations of Greyed-Red Group 180B. Margins: With limited number of stipitate glands.

*Rachis.*—Color: Green Group 137B. Underneath: With limited prickles. Margins: With limited number of stipitate glands.

*Leaflet edge.*—Serrated.

*Shape.*—Generally round. Some ovate.

*Leaflets.*—Number: Many leaves with 7 leaflets.

*Other.*—Moderately glossy. Average thickness.

Disease resistance: Above average resistance to mildew, black spot and Botrytis under normal growing conditions in Half Moon Bay, Calif.

We claim:

1. A new and distinct variety of rose plant of the compact floribunda class, substantially as herein illustrated and described as a distinct and novel rose variety due to its abundant, cherry-red flowers, vigorous and compact growth, year round flowering under glasshouse conditions, suitability for production from softwood cuttings and by traditional budding, and durable flowers and foliage which make the variety suitable for distribution in the floral industry.

* * * * *

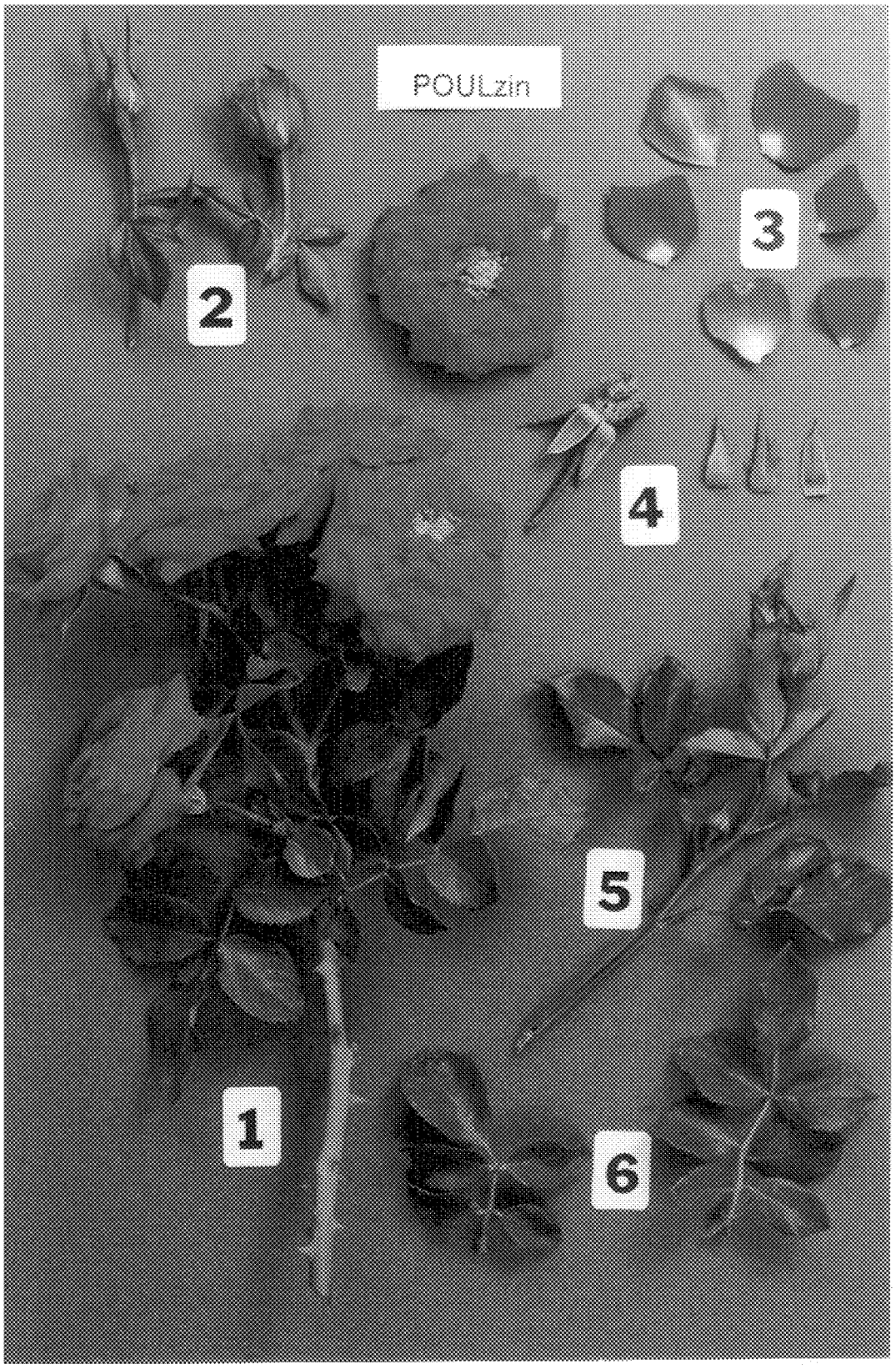
POULzin
2
3
4
5
1
6